United States Patent
Shah et al.

(10) Patent No.: US 8,523,773 B2
(45) Date of Patent: *Sep. 3, 2013

(54) LONG TERM ANALYTE SENSOR ARRAY

(75) Inventors: Rajiv Shah, Rancho Palos Verdes, CA (US); Rebecca K. Gottlieb, Culver City, CA (US); Eric A. Grovender, Minneapolis, MN (US); Shaun M. Pendo, Wofford Heights, CA (US); Paul Citron, New Brighton, MN (US); William P. Van Antwerp, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 945 days.

This patent is subject to a terminal disclaimer.

(21) Appl. No.: 12/503,753

(22) Filed: Jul. 15, 2009

(65) Prior Publication Data
US 2010/0331647 A1 Dec. 30, 2010

Related U.S. Application Data

(62) Division of application No. 10/989,038, filed on Nov. 15, 2004, now Pat. No. 7,577,470.

(60) Provisional application No. 60/519,709, filed on Nov. 13, 2003.

(51) Int. Cl.
*A61B 5/00* (2006.01)

(52) U.S. Cl.
USPC .......................... 600/365; 600/345; 600/347

(58) Field of Classification Search
USPC .......................... 600/309, 347, 365
See application file for complete search history.

(56) References Cited

U.S. PATENT DOCUMENTS

| | | | |
|---|---|---|---|
| 5,672,256 A | 9/1997 | Yee | |
| 5,882,494 A | 3/1999 | Van Antwerp | |
| 5,999,848 A | 12/1999 | Gord et al. | |
| 6,387,048 B1 | 5/2002 | Schulman et al. | |
| 6,477,395 B2 | 11/2002 | Schulman et al. | |
| 6,491,666 B1 | 12/2002 | Santini, Jr. et al. | |
| 6,527,762 B1 | 3/2003 | Santini, Jr. et al. | |
| 6,537,256 B2 | 3/2003 | Santini, Jr. et al. | |

(Continued)

FOREIGN PATENT DOCUMENTS

| | | |
|---|---|---|
| EP | 1145731 | 10/2001 |
| WO | WO 2004/096176 | 11/2004 |
| WO | WO 2005/048834 | 2/2005 |

OTHER PUBLICATIONS

Santini et al., "A controlled-release microchip," Nature 397 (6717), Jan. 28, 1999, pp. 335-338.

*Primary Examiner* — Michael Kahelin
*Assistant Examiner* — Karen Toth
(74) *Attorney, Agent, or Firm* — Gates & Cooper LLP

(57) ABSTRACT

A long term analyte sensor for measuring at least one analyte in the body of a user and which includes a housing, a plurality of analyte contacting sensor elements and at least one structure for relaying information away from the sensor. This plurality of analyte contacting sensor elements are typically disposed in an array. The analyte sensor further includes at least one sensor protection membrane that is controllable in a manner such that sensor elements may be activated (e.g. exposed to the external environment) at different times so as to extend the useful life of the sensor. In illustrative analyte sensors, the analyte is glucose.

16 Claims, 5 Drawing Sheets

(56) References Cited

U.S. PATENT DOCUMENTS

| | | |
|---|---|---|
| 6,551,838 B2 * | 4/2003 | Santini et al. .................. 436/174 |
| 6,656,162 B2 | 12/2003 | Santini, Jr. et al. |
| 6,669,683 B2 | 12/2003 | Santini, Jr. et al. |
| 6,773,429 B2 | 8/2004 | Sheppard, Jr. et al. |
| 6,814,844 B2 | 11/2004 | Bhullar et al. |
| 6,827,250 B2 | 12/2004 | Uhland et al. |
| 6,849,463 B2 | 2/2005 | Santini, Jr. et al. |
| 7,577,470 B2 * | 8/2009 | Shah et al. ..................... 600/345 |
| 2002/0015720 A1 | 2/2002 | Katsarava et al. |
| 2002/0034533 A1 | 3/2002 | Peterson et al. |
| 2003/0199837 A1 | 10/2003 | Vachon |
| 2004/0074785 A1 | 4/2004 | Holker et al. |
| 2004/0106914 A1 | 6/2004 | Coppeta et al. |
| 2004/0247671 A1 | 12/2004 | Prescott et al. |

* cited by examiner

LONG TERM ANALYTE SENSOR ARRAY

CROSS REFERENCE TO RELATED APPLICATIONS

This application is a divisional application of co-pending and commonly-assigned U.S. patent application Ser. No. 10/989,038, filed Nov. 15, 2004, which claims the benefit under 35 U.S.C. §119(e) of U.S. Provisional patent application Ser. No. 60/519,709, filed on Nov. 13, 2003, the contents of which are incorporated by reference.

This application is related to U.S. patent application Ser. No. 10/273,767 filed Oct. 18, 2002 (published as US-2004-0074785-A1) and U.S. patent application Ser. No. 10/861,837, filed Jun. 4, 2004, the contents of both of which are incorporated herein by reference.

BACKGROUND OF THE INVENTION

1. Field of the Invention

The present invention relates generally to analyte sensors for long term use. In certain embodiments, the analyte sensor is for measuring glucose and includes multiple elements that can be replaced or used as other elements are depleted or fail to operate. This expands the longevity of the sensors.

2. Description of Related Art

The assay of biochemical analytes such as glucose and lactate is important in a variety of clinical contexts. For example, the monitoring of glucose concentrations in fluids of the human body is of particular relevance to diabetes management. Continuously or intermittently operating glucose sensors, including sensors implanted in the human body, are sought for the management of diabetes, for example, for warning of imminent or actual hypoglycemia as well as its avoidance. The monitoring of lactate concentrations in fluids of the human body is useful in, but not limited to, the diagnosis and assessment of a number of medical conditions including trauma, myocardial infarction, congestive heart failure, pulmonary edema and septicemia.

Biomedical measuring devices commonly used to monitor physiological variables include amperometric sensor devices that utilize electrodes modified with an appropriate enzyme coating. Sensors having such enzyme electrodes enable the user to determine the concentration of various analytes rapidly and with considerable accuracy, for example by utilizing the reaction of an enzyme and an analyte where this reaction utilizes a detectable coreactant and/or produces a detectable reaction product. For example, a number of glucose sensors have been developed that are based on the reaction between glucose and oxygen that is catalyzed by glucose oxidase (GOx) as shown in FIG. 1. In this context, the accurate measurement of physiological glucose concentrations using sensors known in the art, typically requires that both oxygen and water be present in excess. As glucose and oxygen diffuse into an immobilized enzyme layer on a sensor, the glucose reacts with oxygen to produce $H_2O_2$. Glucose can be detected electrochemically using the immobilized enzyme glucose oxidase coupled to oxygen and/or hydrogen peroxide-sensitive electrodes. The reaction results in a reduction in oxygen and the production of hydrogen peroxide proportional to the concentration of glucose in the sample medium. A typical device is composed of (but not limited to) at least two detecting electrodes, or at least one detecting electrode and a reference signal source, to sense the concentration of oxygen or hydrogen peroxide in the presence and absence of enzyme reaction. Additionally, the complete monitoring system typically contains an electronic sensing and control apparatus for determining the difference in the concentration of the substances of interest. From this difference, the concentration of analytes such as glucose can be determined.

A wide variety of such analyte sensors as well as methods for making and using such sensors are known in the art. Examples of such sensors, sensor sets and methods for their production are described, for example, in U.S. Pat. Nos. 5,390,691, 5,391,250, 5,482,473, 5,299,571, 5,568,806 as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

SUMMARY OF THE INVENTION

Embodiments of the invention disclosed herein provide long term analyte sensors of the type used, for example, in subcutaneous or transcutaneous monitoring of blood glucose levels in a diabetic patient. Embodiments of the invention disclosed herein further provide analyte sensors of the type used, for example, in a variety of clinical contexts such as with dialysis and/or extracorporeal membrane oxygenation protocols. More specifically, the disclosure provided herein teaches optimized long term analyte sensor designs and methods for making and using such sensors.

An illustrative embodiment of the present invention is a long term analyte sensor for measuring at least one analyte in the body of a user and which includes a housing, a plurality of analyte sensor elements and at least one structure for relaying information away from the sensor. This plurality of analyte sensor elements are typically disposed in an array. The analyte sensor further includes at least one sensor protection membrane that is controllable in a manner such that one or more of the plurality of analyte sensor elements may be activated (e.g. exposed to analyte) at different times so as to extend the useful life of the sensor. In alternative embodiments, one or more of the plurality of analyte sensor elements may allow exposure without producing an electrical current until that element is selected to be electrically active.

Another illustrative embodiment of the invention is an analyte sensing device for sensing at least one analyte, the analyte sensing device comprising: a plurality of analyte sensor elements adapted to contact and sense analyte; at least one analyte sensor membrane disposed upon at least one of the plurality of analyte sensor elements in a manner that reversibly prevents an analyte from contacting the at least one of the plurality of analyte sensor elements, wherein the permeability of the analyte sensor membrane can be controlled to allow an analyte to contact at least one of the plurality of analyte sensor elements; and at least one structure operatively coupled to the analyte sensing device for relaying information away from the analyte sensing device. Optionally, the plurality of analyte sensor elements that contact and sense the analyte are disposed in an array in the analyte sensing device. In such devices, the permeability of the analyte sensor membrane is typically controlled so that a second analyte sensor element in the plurality of analyte sensor elements contacts analyte after a first analyte sensor element in the plurality of analyte sensor elements exhibits a decrease in the ability to sense analyte due to biofouling and/or loss of activity of an analyte sensing enzyme disposed in the first analyte sensor element, so that the useful life of the analyte sensing device is extended. In certain embodiments of the invention, the analyte sensing device is implantable within the body of a mammal. In particular embodiments, the analyte is glucose. In alternative embodiments, the analyte is a protein, lactose, a carbohydrate, a saccharide, a mineral, and element, a small molecule compound, a virus, a peptide, a protein fragment, an analogue of a compound, a medication, a drug, an element of a body chemistry assay, body constituent or byproduct, or the like.

As discussed in detail below, the analyte sensor membrane can be made using a number of different methods and materials know in the art. For example, in one embodiment, the analyte sensor membrane comprises a rupturable metallic membrane that hermetically seals the analyte sensor element. Alternatively, the analyte sensor membrane comprises a biodegradable polymer that degrades at a defined rate within an in vivo environment. In certain embodiments of the invention, the analyte sensor membranes and/or the analyte sensing elements are discreetly controlled to allow rupture of a specific membrane and/or interrogation and receipt of signal from a specific analyte sensing element. Optionally, at least one of the analyte sensor elements in the analyte sensing device comprises a hydrogel disposed thereon, wherein upon exposure to an aqueous solution, the hydrogel expands in a manner that increases the permeability of the analyte sensor membrane.

Another embodiment of the invention is a method of making a sensor apparatus for implantation within a mammal comprising the steps of: providing a plurality of analyte sensor elements adapted to contact and sense analyte; providing at least one analyte sensor membrane disposed upon at least one of the plurality of analyte sensor elements in a manner that reversibly prevents an analyte from contacting the at least one of the plurality of analyte sensor elements, wherein the permeability of the analyte sensor membrane can be controlled to allow an analyte to contact at least one of the plurality of analyte sensor elements; and providing at least one structure operatively coupled to the analyte sensing device for relaying information away from the analyte sensing device.

Another embodiment of the invention is a method of sensing an analyte within the body of a mammal, the method comprising implanting an analyte sensor in to the mammal, the analyte sensor comprising: a plurality of analyte sensor elements adapted to contact and sense analyte; at least one analyte sensor membrane disposed upon at least one of the plurality of analyte sensor elements in a manner that reversibly prevents an analyte from contacting the at least one of the plurality of analyte sensor elements, wherein the permeability of the analyte sensor membrane can be controlled to allow an analyte to contact at least one of the plurality of analyte sensor elements; and at least one structure operatively coupled to the analyte sensing device for relaying information away from the analyte sensing device; and sensing an analyte within the body of a mammal.

Yet another embodiment of the invention is a method of extending the useful life of an analyte sensing device comprising analyte sensor elements that exhibit a decrease in the ability to sense analyte over time due to biofouling or a loss of activity of an analyte sensing enzyme disposed on an analyte sensor element; the method comprising sensing an analyte with an analyte sensing device comprising: a plurality of analyte sensor elements adapted to contact and sense analyte; at least one analyte sensor membrane disposed upon at least one of the plurality of analyte sensor elements in a manner that reversibly prevents an analyte from contacting the at least one of the plurality of analyte sensor elements, wherein the permeability of the analyte sensor membrane can be controlled to allow an analyte to contact at least one of the plurality of analyte sensor elements; and at least one structure operatively coupled to the analyte sensing device for relaying information away from the analyte sensing device; wherein the useful life of an analyte sensing device is extended by: deactivating a first analyte sensor element in the plurality of analyte sensor elements that contact and sense analyte when the first analyte sensing element exhibits a decrease in the ability to sense analyte due to biofouling or a loss of activity of an analyte sensing enzyme disposed on the first analyte sensor element; and activating a second analyte sensor element in the plurality of analyte sensor elements adapted to contact and sense analyte by controlling the permeability of an analyte sensor membrane disposed upon the second analyte sensor element to allow an analyte to contact the second analyte sensor element, so that the useful life of the analyte sensing device is extended.

Embodiments of the invention also provide additional articles of manufacture including sensor elements, sensor sets and kits. In one such embodiment of the invention, a kit and/or sensor element or set, useful for the sensing an analyte as is described above, is provided. The kit and/or sensor set typically comprises a container, a label and a sensor as described above. The typical embodiment is a kit comprising a container and, within the container, an analyte sensor apparatus having a design as disclosed herein and instructions for using the analyte sensor apparatus.

Other objects, features and advantages of the present invention will become apparent to those skilled in the art from the following detailed description. It is to be understood, however, that the detailed description and specific examples, while indicating preferred embodiments of the present invention are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

Figure 1:
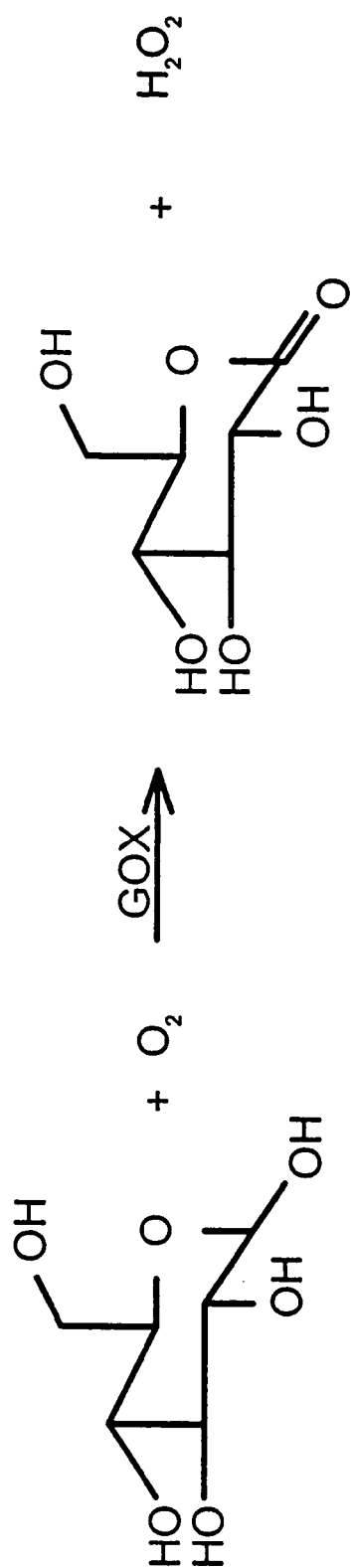
FIG. 1 provides a schematic of the well known reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

Embodiments of the invention disclosed herein provide analyte sensing devices having enhanced material properties such as extended useful lifetimes. The disclosure further provides methods for making and using such sensors. While particular embodiments of the invention pertain to glucose and/or lactate sensors, a variety of the elements disclosed herein (e.g. analyte sensor membranes) can be adapted for use with any one of the wide variety of sensors known in the art. The analyte sensor elements, architectures and methods for making and using these elements that are disclosed herein can be used to establish a variety of sensor structures. Such sensor embodiments of the invention exhibit a surprising degree of flexibility and versatility, characteristic which allow a wide variety of sensor configurations to be designed to examine a wide variety of analyte species.

In typical embodiments of the present invention, the transduction of the analyte concentration into a processable signal is by electrochemical means. These transducers may include any of a wide variety of amperometric, potentiometric, or conductimetric base sensors known in the art. Moreover, the microfabrication sensor techniques and materials of the instant invention may be applied to other types of transducers (e.g., acoustic wave sensing devices, thermistors, gas-sensing electrodes, field-effect transistors, optical and evanescent field wave guides, and the like) fabricated in a substantially nonplanar, or alternatively, a substantially planar manner. A useful discussion and tabulation of transducers which may be exploited in a biosensor as well as the kinds of analytical applications in which each type of transducer or biosensor, in general, may be utilized is found in an article by Christopher R. Lowe in Trends in Biotech. 1984, 2 (3), 59-65.

Specific aspects of embodiments of the invention are discussed in detail in the following sections.

I. Typical Elements, Configurations and Analyte Sensor Embodiments of the Invention A. Sensor Protection Membrane Embodiments of the Invention Long-term (e.g. "prolonged" and "permanent" sensors) analyte sensors such as glucose sensors must operate reliably in harsh environments (e.g. the body) and are often subject to loss of sensitivity for a variety of reasons. These reasons include but are not limited to bio-fouling, loss of enzyme activity due to both environmental and fundamental chemical processes, increases in mass transfer coefficients and macrophage encapsulation. In addition, implanted enzymatic sensors, particularly glucose sensors, need to have a significant amount of enzyme for long-term survival. The difficulty with these implanted sensors is that the large mass of enzyme necessarily acts as a mass transfer barrier, thus increasing the response time.

Embodiments of the invention disclosed herein is designed to address such limitations by teaching analyte sensors having a plurality of sensing elements that are covered by one or more controllable sensor protection membranes. In particular, embodiments of the sensors disclosed herein incorporate one or more sensor protection membranes that are controllable in a manner such that one or more of the plurality of sensor elements may be activated (e.g. exposed to the external environment) at different times during the life of the analyte sensor so as to extend the useful life of the sensor. The analyte sensing protection membranes can take a variety of structural forms (e.g. a film, a layer, a cap etc.) as long as they function to reversibly protect the analyte sensing element of the analyte sensing device from the environment into which the analyte sensing device is placed. Embodiments of the invention disclosed herein further include methods for making the sensors of the invention. The following paragraphs of this section provide a description of typical embodiments of the invention.

One embodiment of the invention is a single chip based sensor that contains a series of individual sensors with limited life-time (weeks to months) that are initially stored inside a hermetically sealed chamber and which can be addressed individually on-demand. In this embodiment of the invention, certain aspects of the sensor are similar to devices used in drug delivery technologies known in the art (see, e.g. U.S. Pat. Nos. 6,551,838, 6,491,666, 6,527,762, U.S. Patent Application No. 20040106914 and Santini, et al. Nature 397, 28 Jan. 1999, the contents of each of which are incorporated by reference). Briefly, in this drug delivery technology, a chip is constructed which contains a large number of reservoirs, each containing a drug. A barrier such as a gold foil membrane covers each reservoir to produce a sealed compartment. When an aliquot of drug is desired, an electrical pulse can delivered to one or more of the foil membrane(s) which results in the drug eluting out of the compartment. In addition, certain embodiments of the invention are similar to serial sensor technologies known in the art and which are described for example in U.S. Pat. No. 5,999,848 which is incorporated herein by reference.

Embodiments of the invention include an analyte sensing device having a plurality of analyte sensor elements that are covered by a barrier membrane (e.g. an analyte sensor membrane). In some embodiments of the invention, the barrier membrane creates a hermetic seal over the analyte sensor element. Certain embodiments of the analyte sensor device provide a long-term implantable sensor with improved characteristics is obtained (e.g. improved mass transfer characteristics). When the analyte sensor membrane covering a particular sensor is controllably permeabilized in a manner similar to that described above, that analyte sensor element then becomes "active" and provides input to an analyte sensing device (e.g. an implanted or an external device), whose performance can be modified by the parameter in question. Should this activated analyte sensor element become unstable or ineffective due to any of a number of reasons (e.g. biofouling), it can be electronically inactivated and another sensor on the analyte sensing device can be activated. Electronic controls for the analyte sensor device can for example incorporate both switching circuits and common electrodes for both reference and counter electrodes.

Applications of embodiments of this invention include continuous sensing of glucose in instances where the analyte sensing element has a limited performance lifetime in the body. In another embodiment of the invention, the analyte sensing device can have a number of sensor platforms (glucose, lactate, pH, oxygen) and different sensors can be activated depending on the medical condition of the patient as determined by some set of existing sensors. For example, in a critical care environment a patient might be monitored for glucose and lactate using a multianalyte sensing device embodiment of the invention. If the glucose signal is stable and the lactate sensor shows an increase in lactate, then pH and $O_2$ analyte sensing elements can be activated to monitor for sepsis. Similarly, analyte sensing elements that are not stable enough for long-term use can be activated only when necessary. Another embodiment of this technology includes monitoring for viral infection (hepatitis, HIV etc.) or cancer during the course of therapy, i.e. one year. In particular, such an analyte sensing device makes discrete counts of viral load (or cancer chemokines or others) on a regular basis. Optionally the analyte sensing device can be implanted near a tumor site or in the liver (for hepatitis) and accessed periodically via external interrogation without the need for concomitant surgeries or invasive tissue testing.

Another embodiment of the invention provides sensor array of analyte sensing elements, optionally within reservoirs/wells and sealed with controllable membranes and which is useful for long term analyte sensing. An illustrative sensor array consists of at least 24 wells in a dielectric skeleton (either patterned with ion beam assisted deposition (IBAD) alumina or drilled into a ceramic substrate), with each sensor element lifetime spanning 2-4 weeks. The base of the well (on a base ceramic with the patterned IBAD alumina wells, or a separate ceramic substrate soldered to the drilled substrate wells) can have a metallized working electrode covered by an immobilized enzyme such as glucose oxidase. The glucose oxidase can be covered by a material such as a Glucose Limiting Membrane (GLM) within the well or on top of the membrane. In a specific example, the well can be hermetically sealed with a gold membrane until programmed voltage-induced dissolution of the membrane. Alternatively, the analyte sensing element can be coated with an expanding hydrogel within the well, such that the voltage-induced dissolution of a portion of the gold membrane induces expansion of the hydrogel, thus mechanically assisting the removal of the membrane from the well's surface. Once the contents of the well are exposed, a working electrode in the analyte sensing element can be individually interrogated. The individual interrogation allows focused sensor readings, while isolating spent sensor elements from obscuring the newly exposed sensor signal. The counter and reference electrodes necessary for electrochemical sensor function may be common to the entire array, or located within each well.

Figure 3:
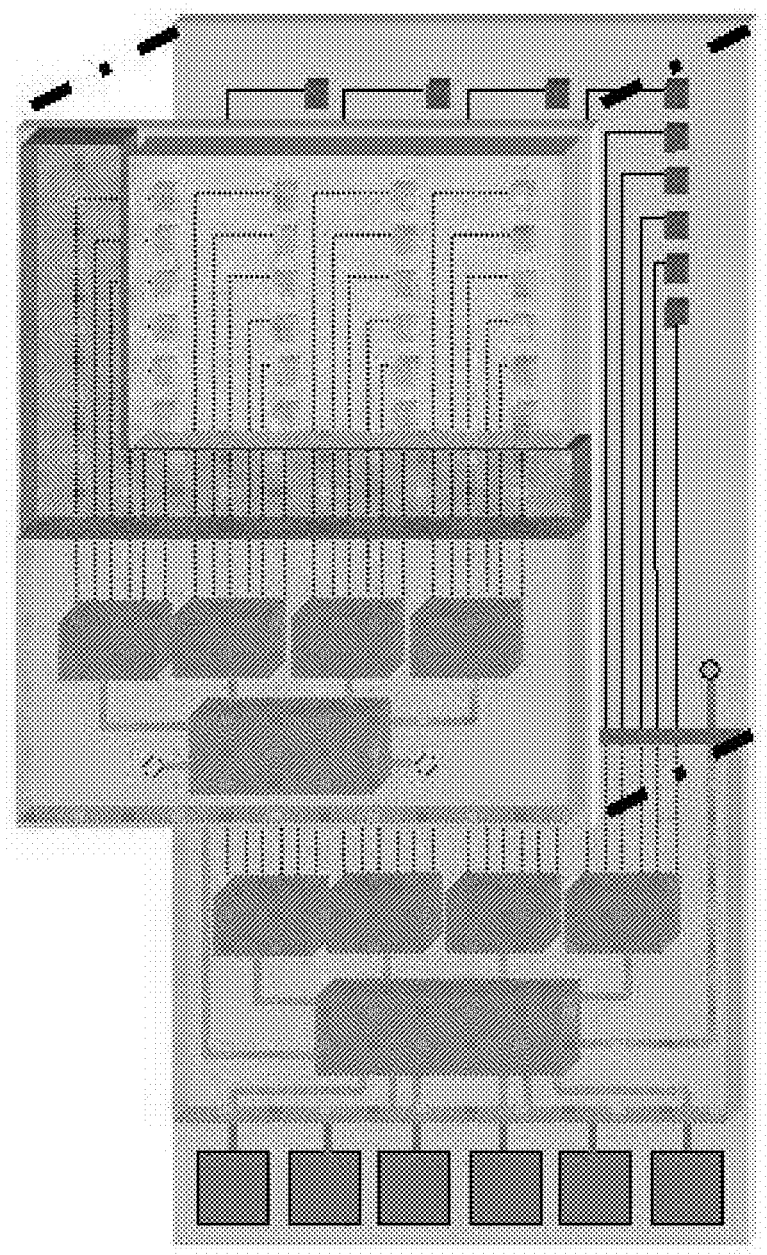
FIG. 3 provides a diagram of a glucose sensor array showing enzyme/membrane array with electronics adhered to electrode array with electronics and lead connections.
Figure 4:
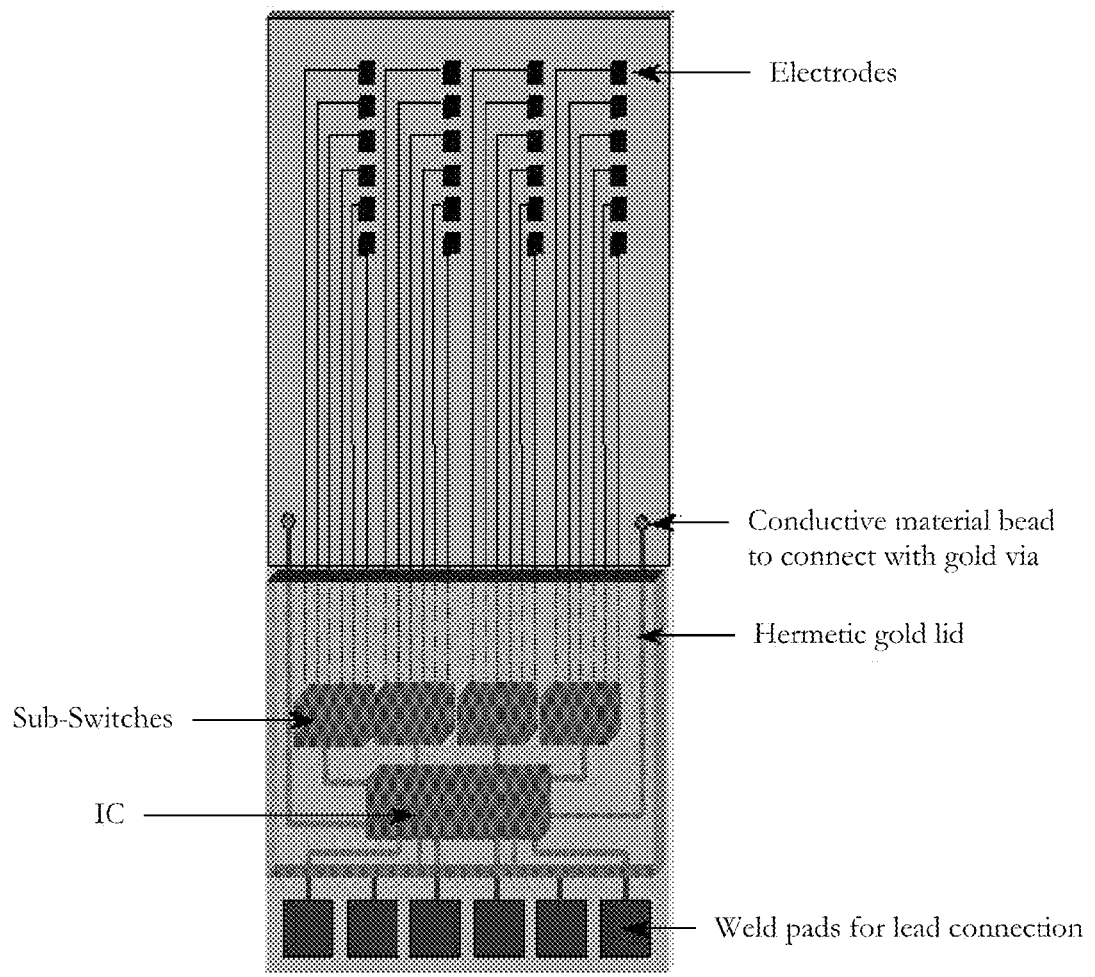
FIG. 4 provides a diagram of a working electrode array with electronics housed under hermetic lid. Power and information is transferred through the lead connection pads to the electronics.
Figure 5:
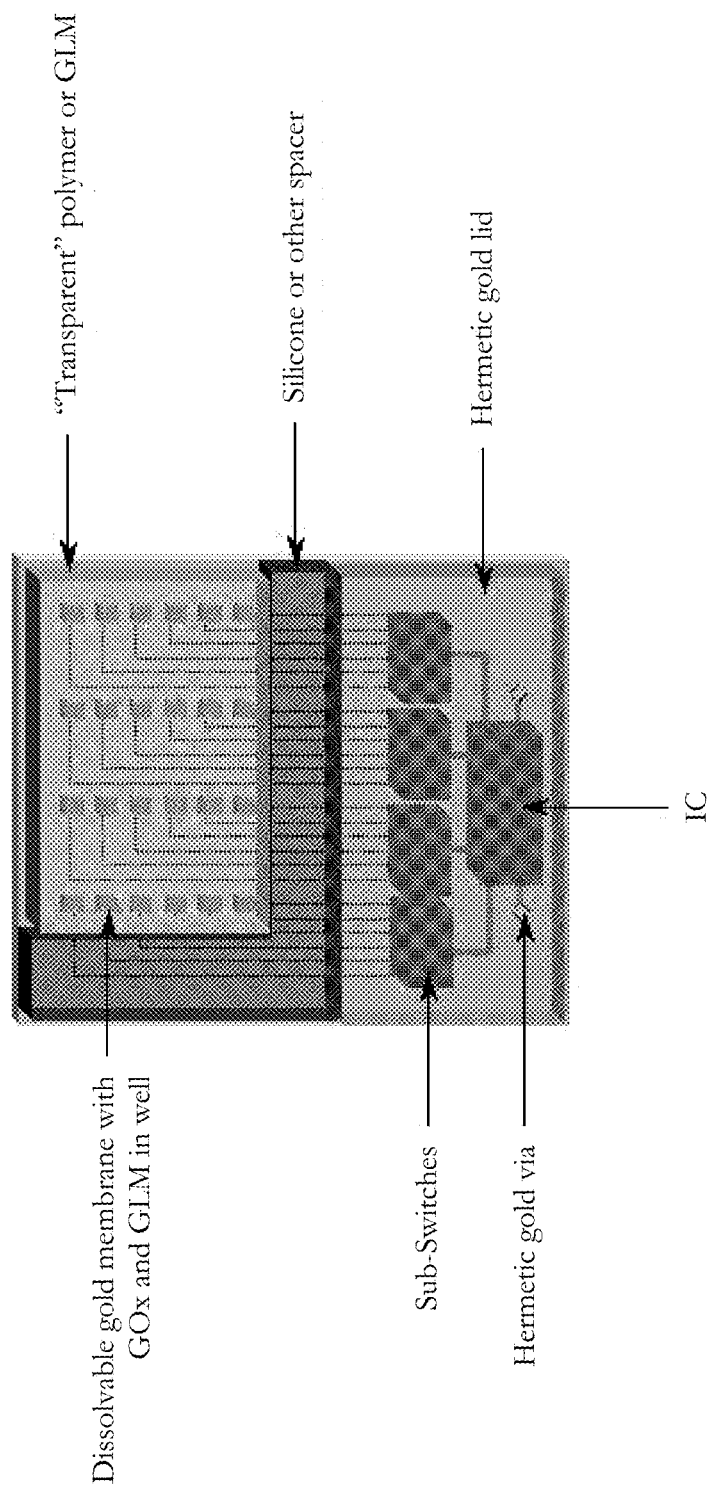
FIG. 5 provides a diagram of an array containing wells filled with enzyme and covered with dissolvable membrane. Electronics for individual addressing are contained under the hermetic lid. Information and power are transferred from the electrode array through hermetic vias.

Addressing of membranes and electrodes in the analyte sensing devices of the invention may be achieved by individual signal traces to each position, or in a similar manner to that used in active matrix display technology. Active matrix addressing utilizes a grid pattern with each addressable position situated at the nodal point. Activation of the appropriate row and column traces will trigger the desired nodal function (electrode reading or membrane dissolution). Addressing of specific traces can be achieved by an integrated circuit, master potentiostat, and a series of programmable digital switches, possibly utilizing hermetic sealing and via technology. Alternatively, the electronics can be packaged at some distant location on the sensor assembly, or separated from the circuitry on an implant unit as is known in the art. Optionally, an analyte sensing device can be programmed to initiate the disintegration or permeabilization of the analyte sensor protective membrane in response to a variety of conditions, including a specific decrease in the function of an active analyte sensor element (e.g. a defined and/or predetermined decrease in function due to biofouling and/or enzyme inactivation) a specific time period, receipt of a signal from another device (for example by remote control or wireless methods), or detection of a particular condition in the environment in which the sensor is placed (e.g. an increase in lactate concentration) Such sensor arrays provide a long term glucose sensor with the dynamic properties of a short term sensor. FIGS. 3-5 provide illustrative embodiments of a sensor array (e.g. a glucose sensor array) with addressable components.

In certain embodiments of the invention, the analyte sensor membrane can be a material that is permeabilizable in response to an applied signal such as an electric field or current, magnetic field, change in pH, or by thermal, chemical, electrochemical, or mechanical signal. Optionally, the analyte sensor membrane can be a rupturable thin metal (e.g., gold) membrane and can be impermeable to the surrounding environment (e.g., body fluids or another chloride containing solution). Based on the type of metal and the surrounding environment, a particular electric potential can be applied to this metal analyte sensor membrane. The metal analyte sensor membrane can then oxidize and dissolve by an electrochemical reaction, "exposing" the contents of the reservoir to the surrounding environment. In addition, materials that normally form insoluble ions or oxidation products in response to an electric potential can be used if, for example, local pH changes near the anode cause these oxidation products to become soluble. Examples of suitable analyte sensor membrane materials include metals such as copper, gold, silver, and zinc, and some polymers known in the art. In another embodiment, the analyte sensor membrane can be a polymer with a specific melting point above body temperature. When the local temperature near the polymer analyte sensor membrane is increased above the polymer's melting point, for example using thin film resistors located near the analyte sensor membrane, the analyte sensor membrane melts and exposes the analyte sensing element to the surrounding environment.

The specific properties of the analyte sensor membrane can be selected based on a variety of factors such as the period over which exposure of the analyte sensing element is desired, generally in the range of weeks to months. In some in vivo embodiments, a single analyte sensing device having a plurality of analyte sensing elements sensors can have the plurality of sensing elements activated sequentially. In this context, by sequentially activating a new sensor as the previously activated sensor loses its ability to sense analyte allows the analyte sensing device to sense analytes for an extended period of time, for example one to twelve months.

In certain embodiments of the invention, the analyte sensor membrane can be made from a material that degrades at a defined rate in an in vitro and/or in vivo environment so that the analyte sensing element is exposed to the analyte upon degradation of this material. A number of such polymers are known in the art and are generally termed biodegradable and/or bioerodable. In this context, at least two types of degradation can occur with such polymers. One type of degradation is bulk degradation, in which the polymer degrades in a fairly uniform manner throughout the matrix. The prevailing mechanism of bulk degradation is hydrolysis of the hydrolytically unstable polymer backbone. First, water penetrates the bulk of the solid polymeric implant, preferentially attacking chemical bonds in the amorphous phase and converting long polymer chains into shorter water-soluble fragments. This results, initially, in a reduction in molecular weight ($M_n$) without an immediate change in physical properties. A second type of degradation is surface erosion, typically called bioerosion. Bioerosion can occur when the rate at which water penetrates the coating of the implant is slower than the rate of the conversion of the polymer into water-soluble materials.

Commonly used biodegradable polymers are typically of the poly(hydroxyacid) type, in particular poly(L-lactic acid), poly(D,L-lactic acid), poly(glycolic acid), and copolymers thereof. A typical copolymer is poly(lactide-co-glycolide), abbreviated as PLGA. These materials are broken down in the body to the non-toxic products lactic acid and glycolic acid, and have been approved by the Food and Drug Administration for use as resorbable sutures, in bone implants, and as controlled release microspheres. Other polymers being utilized include poly(funimaric anhydride) and poly(sebacic anhydride). Mathiowitz, E., Jacob, J. S., Jong, Y. S., Carino, G. P., Chickering, D. E., Chaturvedi, P., Santos, C. A., Vijayaraghavan, K., Montgomery, S., Bassett, M. and Morrell, C., Biologically Erodible Microspheres as Potential Oral Drug Delivery Systems, Nature, 386:410-414, 1997. The use of polymeric microspheres for controlled drug delivery has been the subject of a number of reviews. Langer, R., Cima, L. G., Tamada, J. A. and Wintermantel, E.: "Future Directions in Biomaterials," Biomaterials, 11:738-745, 1990.

Additional illustrative bioerodable and/or biodegradable polymers include polymers and copolymers of: poly(anhydride), poly(hydroxy acid)s, poly(lactone)s, poly(trimethylene carbonate), poly(glycolic acid), poly(lactic acid), poly(glycolic acid)-co-poly(glycolic acid), poly(orthocarbonate), poly(caprolactone), crosslinked biodegradable hydrogel networks like fibrin glue or fibrin sealant, caging and entrapping molecules, like cyclodextrin, molecular sieves and the like. Preferred bioerodable polymers include poly(lactic acid), poly(glycolic acid), poly(lactide), poly(glycolide), poly(lactide-co-glycolide)s, poly(caprolactone), polycarbonates, polyamides, polyanhydrides, poly(amino acid)s, poly(ortho ester)s, polyacetals, polycyanoacrylates, poly(ether ester)s, poly(dioxanone)s, poly(alkylene alkylate)s, copolymers of poly(ethylene glycol) and poly(ortho ester), degradable polyurethanes and copolymers and blends thereof. Illustrative bioerodable polymers are further described in U.S. Patent Application Nos. 20020015720 and 20020034533.

In certain embodiments of the invention, the analyte sensor membrane can be ruptured by physical (i.e., structural) or chemical changes in the analyte sensor membrane material itself, for example, a change caused by a temperature change. For example, the analyte sensor membrane can be made of or include a material that expands when heated. When the analyte sensor membrane is secured in a fixed position and heated, the analyte sensor membrane expands until it cracks or ruptures due to the increase in volume. This embodiment permits heating of the analyte sensor membrane with minimal or no heating of the analyte sensing element, a feature that is particularly important when the analyte sensing element contains heat-sensitive molecules, such as proteins (e.g. glucose oxidase), which can denature upon exposure to excessive heat.

In another embodiment of the invention, the analyte sensor membrane material can melted (i.e., undergoes a phase change) using resistive heating. For in vivo applications, the analyte sensor membrane preferably is composed of biocompatible copolymers, such as organic hydroxy acid derivatives (e.g., lactides and lactones), which can offer a range of selectable melting temperatures (see PCT WO 98/26814). Particular melting temperatures, for example between about 2° C. and about 12° C. above normal body temperature, can be selected for the analyte sensor membranes by proper selection of starting monomer ratios and the resulting molecular weight of the copolymer.

In certain embodiments of the invention, the analyte sensor membrane can be thermally stimulated to enhance degradation. For example, the kinetics of analyte sensor membrane degradation can be very slow at room temperature and the membrane can be essentially stable. However, the kinetics of degradation are significantly increased by increasing the temperature of the membrane material. The absolute rate of degradation can be selected by controlling the composition of the different analyte sensor membrane material that covers the analyte sensing elements. For example, the degradation rate of biocompatible copolymers (e.g., lactones and lactides) can be between several hours and several years, preferably between several weeks to several months, depending on the specific molar ratios of the primary structural units. By using an array of analyte sensor membranes that covers the array of analyte sensing elements, each having a different composition, complex molecular release profiles can be achieved once the device reaches a critical state, for example a state defined by its environment.

In another embodiment of the invention, all analyte sensor membranes have constant disintegration rates (e.g., temperature independent) and the release profile is controlled by selection of the physical dimensions of the analyte sensor membrane material. By fixing the rate of disintegration, the time for membrane disintegration is dependent on the thickness of the analyte sensor membrane material. For example, in an embodiment in which all analyte sensor membranes have identical compositions, molecular release can be controlled by varying the thickness of the membrane.

In certain embodiments of the invention, the analyte sensor membrane is formed of a material having a yield or tensile strength beyond which the material fails by fracture or a material that undergoes a phase change (for example, melts) with selected changes in temperature. The material preferably is selected from metals, such as copper, gold, silver, platinum, and zinc; glasses; ceramics; semiconductors; and brittle polymers, such as semicrystalline polyesters. In particular, the analyte sensor membrane is in the form of a thin film, e.g., a film having a thickness between about 0.1 µm and 1 µm. However, because the thickness depends on the particular material and the mechanism of rupture (i.e., electrochemical vs. mechanical breakdown), thicker analyte sensor membranes, e.g., having a thickness between 1 µm and 100 µm or more, may work better for some materials, such as certain brittle material.

As noted above, the analyte sensor membrane can be made from a plurality of layered materials. For example, the analyte sensor membrane optionally can be coated with an overcoat material to structurally reinforce the rupturable material layer until the overcoat material has been substantially removed by dissolving, eroding, biodegrading, oxidizing, or otherwise degrading, such as upon exposure to water in vivo or in vitro. Representative suitable degradable materials include synthetic or natural biodegradable polymers.

The optimized embodiments of the invention disclosed herein can be universally utilized and/or applied to a wide variety of sensor methods and designs. Consequently, the following sections describe illustrative sensor elements, configurations and methods that can incorporate these embodiments of the invention.

Figure 2:
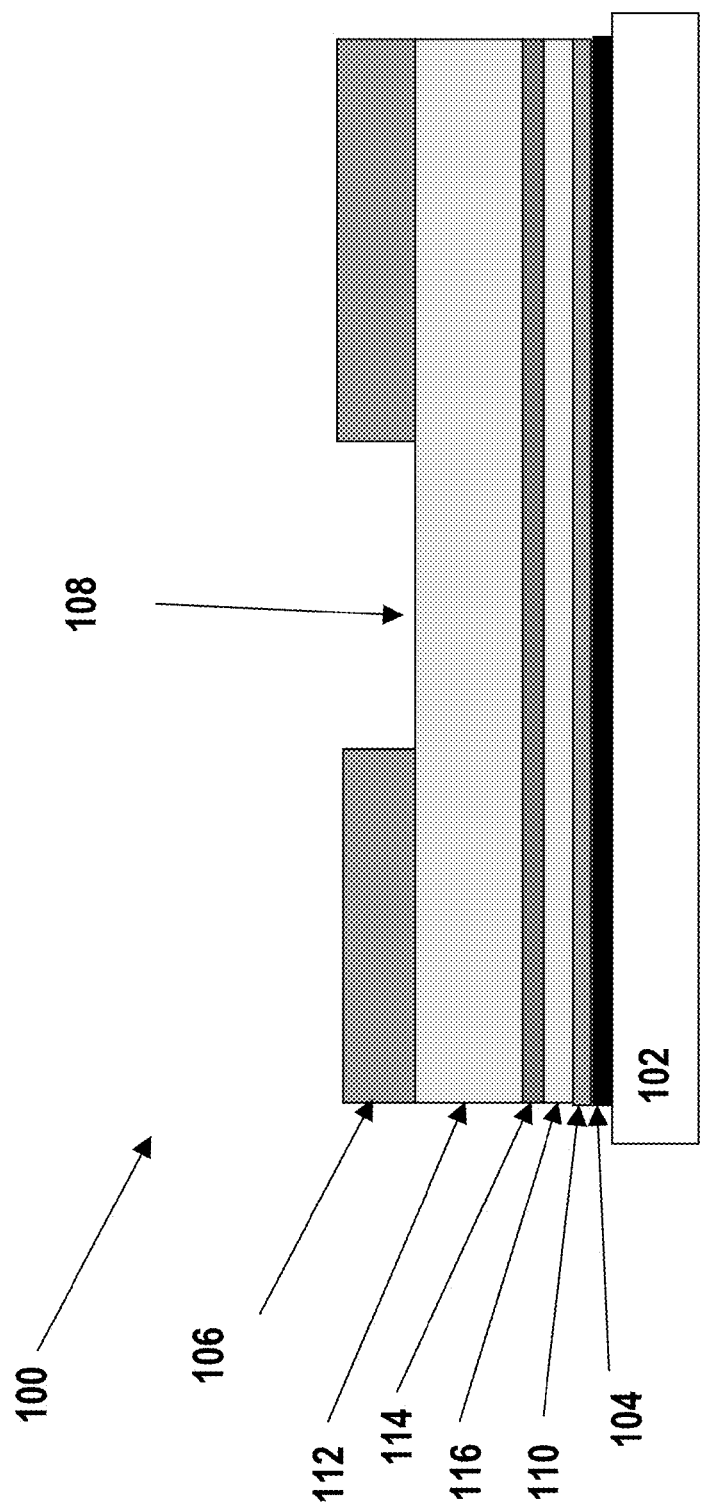
FIG. 2 provides a diagrammatic view of a typical analyte sensing element configuration of an embodiment of the current invention.

B. Diagrammatic Illustration of Typical Analyte Sensor Configuration Embodiments FIG. 2 illustrates a cross-section of a typical analyte sensor element structure 100 of the present invention which is protectable by the sensor protection membranes disclosed herein. The sensor element is formed from a plurality of components that are typically in the form of layers of various conductive and non-conductive constituents disposed on each other according to a method embodiments of the invention to produce a sensor structure. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogenous layers.

The embodiment shown in FIG. 2 includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102.

Typically the conductive layer 104 comprises one or more electrodes. An operating sensor 100 typically includes a plurality of electrodes such as a working electrode, a counter electrode and a reference electrode. Other embodiments may also include an electrode that performs multiple functions, for example one that functions as both as a reference and a counter electrode. Still other embodiments may utilize a separate reference element not formed on the sensor. Typically these electrodes are electrically isolated from each other, while situated in close proximity to one another.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating is optionally disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensor embodiments of the present invention, one or more exposed regions or apertures 108 can be made through the cover layer 106 to open the conductive layer 104 to the external environment and to for example allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2, an analyte sensing layer 110 (which is preferably a sensor chemistry layer, meaning that materials in this layer undergo a chemical reaction to produce a signal that can be sensed by the conductive layer) is disposed on one or more of the exposed electrodes of the conductive layer 104. In particular, the sensor chemistry layer 110 is an enzyme layer. Most preferably, the sensor chemistry layer 110 comprises an enzyme capable of utilizing oxygen and/or producing hydrogen peroxide, for example the enzyme glucose oxidase. Optionally the enzyme in the sensor chemistry layer is combined with a second carrier protein such as human serum albumin, bovine serum albumin or the like. In an illustrative embodiment, an enzyme such as glucose oxidase in the sensor chemistry layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

The analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns ($\mu m$) in thickness, typically the analyte sensing layer is relatively thin as compared to those found in sensors previously described in the art, and is for example, preferably less than 1, 0.5, 0.25 or 0.1 microns in thickness. As discussed in detail below, particular methods for generating a thin analyte sensing layer 110 include spin coating processes, dip and dry processes, low shear spraying processes, ink-jet printing processes, silk screen processes and the like. Most particularly, the thin analyte sensing layer 110 is applied using a spin coating process.

Typically, the analyte sensing layer 110 is coated with one or more additional layers. Optionally, the one or more additional layers includes a protein layer 116 disposed upon the analyte sensing layer 110. Typically, the protein layer 116 comprises a protein such as albumin or the like. Preferably, the protein layer 116 comprises human serum albumin. In particular embodiments of the invention, an additional layer includes an analyte modulating layer 112 that is disposed above the analyte sensing layer 110 to regulate analyte contact with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In typical embodiments of the invention, an adhesion promoter layer 114 is disposed between the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. In particular, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

C. Typical Analyte Sensor Constituent Embodiments

The following disclosure provides examples of typical elements/constituents used in the analyte sensing elements of the invention. While these elements are described as discreet units for purposes of clarity, those of skill in the art understand that sensor can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor).

Base Constituent Embodiments

Sensor embodiments of the invention typically include a base constituent (see, e.g. element 102 in FIG. 2). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as water impermeability and hermeticity. Materials include silicon, metallic, ceramic and polymeric substrates or the like.

The base constituent may be self-supporting or further supported by another material as is known in the art. In one embodiment of the sensor configuration shown in FIG. 2, the base constituent 102 comprises a ceramic. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituent embodiments of the invention can further include other elements known in the art, for example hermetical vias (see, e.g. WO 03/023388). Depending upon the specific sensor design, the base constituent can be relatively thick constituent (e.g. thicker than 25 microns). Alternatively, one can utilize a nonconductive ceramic, such as alumina, in thin constituents, e.g., less than about 25 microns.

Conductive Constituent Embodiments

The electrochemical sensor embodiments of the invention typically include a conductive constituent disposed upon the base constituent that includes at least one electrode for contacting an analyte or its byproduct (e.g. oxygen and/or hydrogen peroxide) to be assayed (see, e.g. element 104 in FIG. 2). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or the reaction product of this interaction (e.g. hydrogen peroxide). Illustrative examples of such elements include electrodes which are capable of producing a variable detectable signals in the presence of variable concentrations of molecules such as hydrogen peroxide or oxygen. Typically, one of these electrodes in the conductive constituent is a working electrode, which can be made from non-corroding metal, conductive polymer or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively, the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensor embodiments of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensor embodiments of the present invention have one or more working electrodes and one or more counter, reference, and/or counter/reference electrodes. One embodiment of the sensor of the present invention has two, three or four or more working electrodes. These working electrodes in he sensor may be integrally connected or they may be kept separate.

Typically, for in vivo use the analyte sensors of the present invention are implanted subcutaneously in the skin of a mammal for direct contact with the body fluids of the mammal, such as blood. Alternatively, the sensors can be implanted into other regions within the body of a mammal such as in the Intraperotineal space. When multiple working electrodes are used, they may be implanted together or at different positions in the body. The counter, reference, and/or counter/reference electrodes may also be implanted either proximate to the working electrode(s) or at other positions within the body of the mammal.

Analyte Sensing Constituent Embodiments

The electrochemical sensor embodiments of the invention include a analyte sensing constituent disposed on the electrodes of the sensor (see, e.g. element 110 in FIG. 2). The term "analyte sensing constituent" is used herein according to art accepted terminology and refers to a constituent comprising a material that is capable of recognizing or reacting with an analyte whose presence is to be detected by the analyte sensor apparatus. Typically, this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA (Human Serum Albumin) mixture. In these typical embodiments, the GOx reacts with glucose present in the sensing environment (e.g. the body of a mammal) and generates hydrogen peroxide according the reaction shown in FIG. 1, wherein the hydrogen peroxide so generated is anodically detected at the working electrode in the conductive constituent. As discussed for example in U.S. patent application Ser. No. 10/273,767 (incorporated herein by reference) extremely thin sensor chemistry constituents are preferred and can be applied to the surface of the electrode matrix by processes known in the art such as spin coating. In an illustrative embodiment, glucose oxidase/albumin is prepared in a physiological solution (e.g., phosphate buffered saline at neutral pH) with the albumin being present in an range of about 0.5%-10% by weight. Optionally the stabilized glucose oxidase constituent that is formed on the analyte sensing constituent is very thin as compared to those previously described in the art, for example less than 2, 1, 0.5, 0.25 or 0.1 microns in thickness. One illustrative embodiment of the invention utilizes a stabilized glucose oxidase constituent for coating the surface of an electrode wherein the glucose oxidase is mixed with a carrier protein in a fixed ratio within the constituent, and the glucose oxidase and the carrier protein are distributed in a substantially uniform manner throughout the constituent. In particular, the constituent is less than 2 microns in thickness. Surprisingly, sensors having these extremely thin analyte sensing constituents have material properties that exceed those of sensors having thicker coatings including enhanced longevity, linearity, regularity as well as improved signal to noise ratios. While not being bound by a specific scientific theory, it is believed that sensors having extremely thin analyte sensing constituents have surprisingly enhanced characteristics as compared to those of thicker constituents because in thicker enzyme constituents only a fraction of the reactive enzyme within the constituent is able to access the analyte to be sensed. In sensors utilizing glucose oxidase, the thick coatings produced by electrodeposition may hinder the ability of hydrogen peroxide generated at the reactive interface of a thick enzyme constituent to contact the sensor surface and thereby generate a signal.

As noted above, the enzyme and the second protein are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is a preferred crosslinking reagent, other cross-linking reagents may also be used or may be used in place of glutaraldehyde, including, but not limited to, an amine reactive, homofunctional, cross-linking reagent such as Disuccinimidyl Suberate (DSS). Another example is 1-Ethyl-3 (3-Dimethylaminopropyl) Carbodiimide (EDC), which is a zero-length cross-linker. EDC forms an amide bond between carboxylic acid and amine groups. Other suitable cross-linkers also may be used, as will be evident to those skilled in the art.

The GOx and/or carrier protein concentration may vary for different embodiments of the invention. For example, the GOx concentration may be within the range of approximately 50 mg/ml (approximately 10,000 U/ml) to approximately 700 mg/ml (approximately 150,000 U/ml). In particular, the GOx concentration is about 115 mg/ml (approximately 22,000 U/ml). In such embodiments, the HSA concentration may vary between about 0.5%-30% (w/v), depending on the GOx concentration. In particular, the HSA concentration is about 1-10% w/v, and most particularly is about 5% w/v. In alternative embodiments of the invention, collagen or BSA (Bovine Serum Albumin) or other structural proteins used in these contexts can be used instead of or in addition to HSA. Although GOx is discussed as an enzyme in the analyte sensing constituent, other proteins and/or enzymes may also be used or may be used in place of GOx, including, but not limited to glucose dehydrogenase or hexokinase, hexose oxidase, lactate oxidase, and the like. Other proteins and/or enzymes may also be used, as will be evident to those skilled in the art. Moreover, although HSA is employed in the example embodiment, other structural proteins, such as BSA, collagens or the like, can be used instead of or in addition to HSA.

For embodiments employing enzymes other than GOx, concentrations other than those discussed herein may be utilized. For example, depending on the enzyme employed, concentrations ranging from approximately 10% weight per weight to 70% weight per weight may be suitable. The concentration may be varied not only depending on the particular enzyme being employed, but also depending on the desired properties of the resulting protein matrix. For example, a certain concentration may be utilized if the protein matrix is to be used in a diagnostic capacity while a different concentration may be utilized if certain structural properties are desired. Those skilled in the art will understand that the concentration utilized may be varied through experimentation to determine which concentration (and of which enzyme or protein) may yield the desired result.

As noted above, in particular embodiments of the invention, the analyte sensing constituent includes a composition (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In certain embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the preferred sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; (Jan. 7, 1991) the entire contents of which are incorporated herein by reference.

Other useful analyte sensing constituents can be formed to include antibodies whose interaction with a target analyte is capable of producing a detectable signal that can be sensed by the electrically conductive elements after interacting with the target analyte whose presence is to be detected. For example U.S. Pat. No. 5,427,912 (which is incorporated herein by reference) describes an antibody-based apparatus for electrochemically determining the concentration of an analyte in a sample. In this device, a mixture is formed which includes the sample to be tested, an enzyme-acceptor polypeptide, an enzyme-donor polypeptide linked to an analyte analog (enzyme-donor polypeptide conjugate), a labeled substrate, and an antibody specific for the analyte to be measured. The analyte and the enzyme-donor polypeptide conjugate competitively bind to the antibody. When the enzyme-donor polypeptide conjugate is not bound to antibody, it will spontaneously combine with the enzyme acceptor polypeptide to form an active enzyme complex. The active enzyme then hydrolyzes the labeled substrate, resulting in the generation of an electroactive label, which can then be oxidized at the surface of an electrode. A current resulting from the oxidation of the electroactive compound can be measured and correlated to the concentration of the analyte in the sample. U.S. Pat. No. 5,149,630 (which is incorporated herein by reference) describes an electrochemical specific binding assay of a ligand (e.g., antigen, hapten or antibody) wherein at least one of the components is enzyme-labelled, and which includes the step of determining the extent to which the transfer of electrons between the enzyme substrate and an electrode, associated with the substrate reaction, is perturbed by complex formation or by displacement of any ligand complex relative to unbound enzyme-labelled component. The electron transfer is aided by electron-transfer mediators which can accept electrons from the enzyme and donate them to the electrode or vice versa (e.g. ferrocene) or by electron-transfer promoters which retain the enzyme in close proximity with the electrode without themselves taking up a formal charge. U.S. Pat. No. 5,147,781 (which is incorporated herein by reference) describes an assay for the determination of the enzyme lactate dehydrogenase-5 (LDH5) and to a biosensor for such quantitative determination. The assay is based on the interaction of this enzyme with the substrate lactic acid and nicotine-amine adenine dinucleotide (NAD) to yield pyruvic acid and the reduction product of NAD. Anti-LDH5 antibody is bound to a suitable glassy carbon electrode, this is contacted with the substrate containing LDH5, rinsed, inserted into a NAD solution, connected to an amperometric system, lactic acid is added and the current changes are measured, which are indicative of the quantity of LDH-5. U.S. Pat. No. 6,410,251 (which is incorporated herein by reference) describes an apparatus and method for detecting or assaying one constituting member in a specific binding pair, for example, the antigen in an antigen/antibody pair, by utilizing specific binding such as binding between an antigen and an antibody, together with redox reaction for detecting a label, wherein an oxygen micro-electrode with a sensing surface area is used. In addition, U.S. Pat. No. 4,402,819 (which is incorporated herein by reference) describes an antibody-selective potentiometric electrode for the quantitative determination of antibodies (as the analyte) in dilute liquid serum samples employing an insoluble membrane incorporating an antigen having bonded thereto an ion carrier effecting the permeability of preselected cations therein, which permeability is a function of specific antibody concentrations in analysis, and the corresponding method of analysis. For related disclosures, see also U.S. Pat. Nos. 6,703,210, 5,981,203, 5,705,399 and 4,894,253, the contents of which are incorporated herein by reference.

In addition to enzymes and antibodies, other exemplary materials for use in the analyte sensing constituents of the sensors disclosed herein include polymers that bind specific types of cells or cell components (e.g. polypeptides, carbohydrates and the like); single-strand DNA; antigens and the like. The detectable signal can be, for example, an optically detectable change, such as a color change or a visible accumulation of the desired analyte (e.g., cells). Sensing elements can also be formed from materials that are essentially non-reactive (i.e., controls). The foregoing alternative sensor elements are beneficially included, for example, in sensors for use in cell-sorting assays and assays for the presence of pathogenic organisms, such as viruses (HIV, hepatitis-C, etc.), bacteria, protozoa and the like.

Also contemplated are analyte sensors that measure an analyte that is present in the external environment and that can in itself produce a measurable change in current at an electrode. In sensors measuring such analytes, the analyte sensing constituent can be optional.

Protein Layer Constituent Embodiments

The electrochemical sensor embodiments of the invention optionally include a protein layer constituent disposed between the analyte sensing constituent and the analyte modulating constituent (see, e.g. element 116 in FIG. 2). The term "protein layer constituent" is used herein according to art accepted terminology and refers to constituent containing a carrier protein or the like that is selected for compatibility with the analyte sensing constituent and or the analyte modulating constituent. In typical embodiments, the protein constituent comprises an albumin such as human serum albumin (HSA). The HSA concentration may vary between about 0.5%-30% (w/v). Preferably the HSA concentration is about 1-10% w/v, and most preferably is about 5% w/v. In alternative embodiments of the invention, collagen or BSA (Bovine Serum Albumin) or other structural proteins used in these contexts can be used instead of or in addition to HSA. This constituent is typically crosslinked on the analyte sensing constituent according to art accepted protocols.

Adhesion Promoting Constituent Embodiments

The electrochemical sensor embodiments of the invention can include one or more adhesion promoting (AP) constituents (see, e.g. element 114 in FIG. 2). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. In particular, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. In particular, the adhesion promoter constituent comprises a silane compound such as γ-aminopropyltrimethoxysilane.

The use of silane coupling reagents, especially those of the formula R'Si(OR)$_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase (GO$_x$) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% polydimethyl siloxane (PDMS), preferably 5-15% PDMS, and most preferably 10% PDMS. In other embodiments of the invention, the adhesion promoting constituent includes an agent selected for its ability to crosslink a siloxane moiety present in a proximal constituent such as the analyte modulating constituent. In closely related embodiments of the invention, the adhesion promoting constituent includes an agent selected for its ability to crosslink an amine or carboxyl moiety of a protein present in a proximal constituent such a the analyte sensing constituent and/or the protein constituent.

Analyte Modulating Constituent Embodiments

The electrochemical sensor embodiments of the invention include an analyte modulating constituent disposed on the sensor (see, e.g. element 112 in FIG. 2). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte limiting membrane which operates to prevent or restrict the diffusion of one or more analytes, such as glucose, through the constituents. In other embodiments of the invention, the analyte modulating constituent operates to facilitate the diffusion of one or more analytes, through the constituents. Optionally, such analyte modulating constituents can be formed to prevent or restrict the diffusion of one type of molecule through the constituent (e.g. glucose), while at the same time allowing or even facilitating the diffusion of other types of molecules through the constituent (e.g. O$_2$).

With respect to glucose sensors, in known enzyme electrodes, glucose and oxygen from blood, as well as some interferants, such as ascorbic acid and uric acid diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose through. In this context, an analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868 and 5,391,250, the disclosures of each being incorporated herein by reference. The hydrogels described therein are particularly useful with a variety of implantable devices for which it is advantageous to provide a surrounding water constituent. In certain embodiments of the invention, the analyte modulating composition includes polydimethyl siloxane (PDMS). In other embodiments of the invention, the analyte modulating constituent includes an agent selected for its ability to crosslink a siloxane moiety present in a proximal constituent. In closely related embodiments of the invention, the adhesion promoting constituent includes an agent selected for its ability to crosslink an amine or carboxyl moiety of a protein present in a proximal constituent.

Cover Constituent Embodiments

The electrochemical sensor embodiments of the invention include one or more cover constituents which are typically electrically insulating protective constituents (see, e.g. element 106 in FIG. 2). Typically, such cover constituents are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Various illustrative embodiments of the invention and their characteristics are discussed in detail in the following sections.

D. Illustrative Embodiments of Analyte Sensor Apparatus and Associated Characteristics The analyte sensor apparatus disclosed herein has a number of embodiments. A general embodiment of the invention is an analyte sensor apparatus for implantation within a mammal. While the analyte sensors are typically designed to be implantable within the body of a mammal, the sensor are not limited to any particular environment can instead be used in a wide variety of contexts, for example for the analysis of most liquid samples including biological fluids such as whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

As noted above, the sensor embodiments disclosed herein can be used to sense analytes of interest in one or more physiological environments. In certain embodiments for example, the sensor can be in direct contact with interstitial fluids as typically occurs with subcutaneous sensors. The sensors of the present invention may also be part of a skin surface system where interstitial glucose is extracted through the skin and brought into contact with the sensor (see, e.g. 6,155,992 and 6,706,159 which are incorporated herein by reference). In other embodiments, the sensor can be in contact with blood as typically occurs for example with intravenous sensors. The sensor embodiments of the invention further include those adapted for use in a variety of contexts. In certain embodiments for example, the sensor can be designed for use in mobile contexts, such as those employed by ambulatory users. Alternatively, the sensor can be designed for use in stationary contexts such as those adapted for use in clinical settings. Such sensor embodiments include for example those used to monitor one or more analytes present in one or more physiological environments in a hospitalized patient.

Sensor embodiments of the invention can also be incorporated in to a wide variety of medical systems known in the art. Sensor embodiments of the invention can be used for example in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. In particular, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Certain embodiments of the invention measure peroxide and have the advantageous characteristic of being suited for implantation in a variety of sites in the mammal including regions of subcutaneous implantation and intravenous implantation as well as implantation into a variety of non-vascular regions. A peroxide sensor design that allows implantation into non-vascular regions has advantages over certain sensor apparatus designs that measure oxygen due to the problems with oxygen noise that can occur in oxygen sensors implanted into non-vascular regions. For example in such implanted oxygen sensor apparatus designs, oxygen noise at the reference sensor can compromise the signal to noise ratio which consequently perturbs their ability to obtain stable glucose readings in this environment. The peroxide sensor embodiments of the invention therefore overcome the difficulties observed with such oxygen sensors in non-vascular regions.

Certain embodiments of the invention provide advantageous long term or "permanent" sensors which are suitable for implantation in a mammal for a time period of greater than 30 days. In particular, as is known in the art (see, e.g. ISO 10993, Biological Evaluation of Medical Devices) medical devices such as the sensors described herein can be categorized into three groups based on implant duration: (1) "Limited" (<24 hours), (2) "Prolonged" (24 hours-30 days), and (3) "Permanent" (>30 days). In particular embodiments of the invention, the design of the peroxide sensor of the invention allows for a "Permanent" implantation according to this categorization, i.e. >30 days. In related embodiments of the invention, the highly stable design of the peroxide sensor of the invention allows for an implanted sensor to continue to function in this regard for 2, 3, 4, 5, 6 or 12 or more months.

The invention disclosed herein has a number of embodiments. A typical embodiment of the invention is a long term sensor for measuring at least one analyte in the body of a user, the sensor including: a housing; a sensor coupled to the housing; at least one structure operatively coupled to the sensor for relaying information away from the sensor, where the sensor includes at least one sensor array having two or more elements that is controllable in a manner such that sensor elements may be activated at different times to extend the useful life of the sensor. In certain embodiments of the invention, such long term analyte sensing devices are prolonged analyte sensors. Alternatively, the analyte sensing devices are permanent analyte sensors.

Another illustrative embodiment of the invention is an analyte sensing device for sensing at least one analyte, the analyte sensing device including: a plurality of analyte sensor elements adapted to contact and sense analyte; at least one analyte sensor membrane disposed upon at least one of the plurality of analyte sensor elements in a manner that reversibly prevents an analyte from contacting the at least one of the plurality of analyte sensor elements, where the permeability of the analyte sensor membrane can be controlled to allow an analyte to contact at least one of the plurality of analyte sensor elements; and at least one structure operatively coupled to the analyte sensing device for relaying information away from the analyte sensing device. Optionally, the plurality of analyte sensor elements that contact and sense the analyte are disposed in an array in the analyte sensing device.

Individual sensor elements within the plurality of the analyte sensor elements in the analyte sensing device can sense the same or different analytes. In this context, embodiments of the invention are adapted to measure multiple analytes simultaneously. For example, embodiments of the inventions can be adapted so that multiple individual sensor elements (e.g. those within each cavity) adapted to sense different analytes can be exposed to the external environment at the same time. Alternatively, multiple individual sensor elements adapted to sense different analytes can be exposed to the external environment at different times. Similar embodiments include an analyte sensing device adapted to function as multi-analyte sensor on a single chip (or, alternatively, on multiple chips). In certain contexts, a signal from an individual analyte sensor element within the plurality of analyte sensor elements that contact and sense an analyte in the analyte sensing device are individually interrogated and/or read. Alternatively, multiple analyte sensor elements within the plurality of analyte sensor elements that contact and sense an analyte in the analyte sensing device are interrogated and/or read simultaneously and/or in combination.

Embodiments of the analyte sensing device include those adapted to include both analyte sensing elements covered by a analyte sensor membrane and, in addition, include one or more reservoirs that are also covered by a controllable analyte sensor membrane and which contain one or more compounds that can be controllably released from the reservoir to, for example, facilitate the activity of the analyte sensing device. In one such embodiment, such reservoirs can include solutions that function as calibration fluids (e.g. fluids having defined analyte concentrations) for an analyte sensing element within the analyte sensing device. Examples of such calibration fluids include fluids containing define glucose and/or lactate concentrations (i.e. for glucose and/or lactate sensors). In such embodiments of the invention, a calibration fluid from one or more reservoirs can be released in a manner that exposes them to the analyte sensing element(s) in the device and in this way calibrate each of the analyte sensors. In certain embodiments of the invention, cavities containing such fluids can be co-localized with the sensing elements.

Embodiments of the invention that are adapted to include barrier membranes that reversibly cover both analyte sensing elements as well reservoirs containing compounds that can be controllably released into the environment, include those where the compounds in the reservoirs are designed to enhance the function of the analyte sensing device by, for example, reshaping and/or adapting the in vivo tissue environment into which the sensing device is placed. In one such embodiment of the invention, the reservoir can contain a compound that is designed to decrease the host response that can occur with the implantation of medical devices. Such compounds can include any one of a wide variety of such compounds known in the art, for example hormones that decrease cellular responses and/or antibiotics such as rapamycin. Such compounds include "growth inhibitory agents" which are compounds or compositions which inhibit growth of a cell in vitro and/or in vivo. Thus, illustrative growth inhibitory agent may be those which significantly reduce the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C In alternative embodiments of the invention, the reservoir can contain a compound designed effect the implantation site, for example to enhance "vascularity" at a tissue site in a manner that enhances the transport of analyte to the analyte sensing element. Such compounds can include any one of a wide variety of such compounds known in the art, for example cytokines. In this context, "cytokine" means those proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

Other embodiments of the invention include those where the reservoir can contain a series of compounds that are released at different times in a manner that enhances drug delivery an/or the tissue environment surrounding a device to create the most optimal environment. As subcutaneous and peritoneal tissue are well known for aggressive host response—certain embodiments of the invention include compounds that diminish the host response in the immediate period post implantation (e.g. the first few hours) through some drug; and then subsequently promote blood vessel formation near the implant during the extended period post implantation (e.g. the next few weeks), while at the same time minimizing a potential fibrous capsule formation. In such embodiments, various reservoirs in the analyte sensing device can contain a series of different compounds that are released according to a predetermined drug profile.

In certain embodiments of the invention, the analyte sensing element in the analyte sensor device/apparatus includes, but is not limited to, a base layer and a conductive layer disposed upon the base layer where the conductive layer includes a working electrode and preferably a reference electrode and a counter electrode. In this embodiment of the invention, an analyte sensing layer is disposed on the conductive layer. Typically, the analyte sensing layer comprises a composition that detectably alters the electrical current at the working electrode in the conductive layer in the presence of an analyte. Illustrative examples of such compositions include enzymes such as glucose oxidase, glucose dehydrogenase, lactate oxidase, hexokinase and lactose dehydrogenase or the like (e.g. any other protein and/or polymer and/or a combination thereof that stabilizes the enzyme layer). This embodiment of the invention optionally includes a protein layer disposed on the analyte sensing layer, with this protein layer typically including a carrier protein such as bovine serum albumin or human serum albumin or the like. In this embodiment, an adhesion promoting layer is disposed on the analyte sensing layer or the optional protein layer, which serves to promotes the adhesion between the analyte sensing layer and one or more proximal sensor layers. In particular, this adhesion promoting layer includes a silane composition selected for its ability to enhance the stability of the sensor structure, for example γ-aminopropyltrimethoxysilane. This embodiment also includes an analyte modulating layer disposed above the analyte sensing layer, where the analyte modulating layer modulates the diffusion of the analyte through, for example a glucose limiting membrane. This embodiment also includes a insulative cover layer disposed on at least a portion of the analyte modulating layer, where the cover layer further includes an aperture that exposes at least a portion of the analyte modulating layer to a solution comprising the analyte to be sensed. In particular, the analyte sensor apparatus is designed to function via anodic polarization such that the alteration in current can be detected at the working electrode (anode) in the conductive layer of the analyte sensor apparatus; and the alteration in current that can be detected at this working anode can be correlated with the concentration of the analyte.

In the device embodiments of the invention, the permeability of the analyte sensor membrane is typically controlled so that a second analyte sensor element in the plurality of analyte sensor elements contacts analyte after a first analyte sensor element in the plurality of analyte sensor elements exhibits a decrease in the ability to sense analyte due to biofouling and/or loss of activity of an analyte sensing enzyme disposed in the first analyte sensor element, so that the useful life of the analyte sensing device is extended. In certain embodiments of the invention, the analyte sensing device is implantable within the body of a mammal. Optionally, the analyte sensed is glucose and/or lactate.

As discussed in detail below, the analyte sensor membrane can be made using a number of different methods and materials know in the art. For example, in one embodiment, the analyte sensor membrane comprises a rupturable metallic membrane that hermetically seals the analyte sensor element. Alternatively, the analyte sensor membrane comprises a biodegradable polymer that degrades at a defined rate within an in vivo environment.

In certain embodiments of the invention, the analyte sensor membranes and/or the analyte sensing elements are discreetly controlled to allow rupture of a specific membrane and/or interrogation and receipt of signal from a specific analyte sensing element. In certain embodiments of the invention, the plurality of analyte sensor elements has a plurality of different analyte sensor membranes disposed thereon. Alternatively, the plurality of analyte sensor elements have similar or identical analyte sensor membranes disposed thereon. Optionally, at least one of the analyte sensor elements in the analyte sensing device comprises a hydrogel disposed thereon, wherein upon exposure to an aqueous solution, the hydrogel expands in a manner that increases the permeability of the analyte sensor membrane.

Another embodiment of the invention is a method of making a sensor apparatus for implantation within a mammal including the steps of: providing a plurality of analyte sensor elements adapted to contact and sense analyte; providing at least one analyte sensor membrane disposed upon at least one of the plurality of analyte sensor elements in a manner that reversibly prevents an analyte from contacting the at least one of the plurality of analyte sensor elements, where the permeability of the analyte sensor membrane can be controlled to allow an analyte to contact at least one of the plurality of analyte sensor elements; and providing at least one structure operatively coupled to the analyte sensing device for relaying information away from the analyte sensing device.

Yet another embodiment of the invention is a method of extending the useful life of an analyte sensing device including analyte sensor elements that exhibit a decrease in the ability to sense analyte over time due to biofouling or a loss of activity of an analyte sensing enzyme disposed on an analyte sensor element; the method including sensing an analyte with an analyte sensing device including: a plurality of analyte sensor elements adapted to contact and sense analyte; at least one analyte sensor membrane disposed upon at least one of the plurality of analyte sensor elements in a manner that reversibly prevents an analyte from contacting the at least one of the plurality of analyte sensor elements, where the permeability of the analyte sensor membrane can be controlled to allow an analyte to contact at least one of the plurality of analyte sensor elements; and at least one structure operatively coupled to the analyte sensing device for relaying information away from the analyte sensing device; where the useful life of an analyte sensing device is extended by: deactivating a first analyte sensor element in the plurality of analyte sensor elements that contact and sense analyte when the first analyte sensing element exhibits a decrease in the ability to sense analyte due to biofouling or a loss of activity of an analyte sensing enzyme disposed on the first analyte sensor element; and activating a second analyte sensor element in the plurality of analyte sensor elements adapted to contact and sense analyte by controlling the permeability of an analyte sensor membrane disposed upon the second analyte sensor element to allow an analyte to contact the second analyte sensor element, so that the useful life of the analyte sensing device is extended.

The various components of the analyte sensing devices disclosed herein can be arranged in a variety of configurations. For example in certain embodiments of the invention, at least one of the plurality of analyte sensor elements is disposed in a reservoir or well. Alternatively, at least one of the plurality of analyte sensor elements is not disposed in a reservoir or well. This second configuration is favored for example in situations where a reservoir or well structure in an implantable analyte sensing device acts as a trap for debris (e.g. cellular components etc.) that accelerates biofouling of an analyte sensor elements. Consequently, by eliminating the reservoir or well, for example by having the analyte sensing element flush with a housing in which it is placed, biofouling of the analyte sensing elements is inhibited.

E. Permutations of Analyte Sensor Apparatus and Element Embodiments

As noted above, the invention disclosed herein encompasses a variety of sensor embodiments, all of which can be covered by one or more sensor protection membranes. Such embodiments of the invention allow artisans to generate a variety of permutations of the analyte sensor apparatus disclosed herein. As noted above, illustrative general embodiments of the sensor disclosed herein include a base layer, a cover layer and at least one layer having a sensor element such as an electrode disposed between the base and cover layers. Typically, an exposed portion of one or more sensor elements (e.g., a working electrode, a counter electrode, reference electrode, etc.) is coated with a very thin layer of material having an appropriate electrode chemistry. For example, an enzyme such as lactate oxidase, glucose oxidase, glucose dehydrogenase or hexokinase, can be disposed on the exposed portion of the sensor element within an opening or aperture defined in the cover layer. FIG. 2 illustrates a cross-section of a typical sensor structure 100 of the present invention. The sensor is formed from a plurality of layers of various conductive and non-conductive constituents disposed on each other according to a method of the invention to produce a sensor structure 100.

As noted above, in the sensors of the invention, the various layers (e.g. the analyte sensing layer) of the sensors can have one or more bioactive and/or inert materials incorporated therein. The term "incorporated" as used herein is meant to describe any state or condition by which the material incorporated is held on the outer surface of or within a solid phase or supporting matrix of the layer. Thus, the material "incorporated" may, for example, be immobilized, physically entrapped, attached covalently to functional groups of the matrix layer(s). Furthermore, any process, reagents, additives, or molecular linker agents which promote the "incorporation" of said material may be employed if these additional steps or agents are not detrimental to, but are consistent with the objectives of the present invention. This definition applies, of course, to any of the embodiments of the present invention in which a bioactive molecule (e.g. an enzyme such as glucose oxidase) is "incorporated." For example, Certain layers of the sensors disclosed herein include a proteinaceous substance such as albumin which serves as a crosslinkable matrix. As used herein, a proteinaceous substance is meant to encompass substances which are generally derived from proteins whether the actual substance is a native protein, an inactivated protein, a denatured protein, a hydrolyzed species, or a derivatized product thereof. Examples of suitable proteinaceous materials include, but are not limited to enzymes such as glucose oxidase and lactate oxidase and the like, albumins (e.g. human serum albumin, bovine serum albumin etc.), caseins, gamma-globulins, collagens and collagen derived products (e.g., fish gelatin, fish glue, animal gelatin, and animal glue).

A particular embodiment of the invention is shown in FIG. 2. This embodiment includes an electrically insulating base layer 102 to support the sensor 100. The electrically insulating layer base 102 can be made of a material such as a ceramic substrate, which may be self-supporting or further supported by another material as is known in the art. In an alternative embodiment, the electrically insulating layer 102 comprises a polyimide substrate, for example a polyimide tape, dispensed from a reel. Providing the layer 102 in this form can facilitate clean, high density mass production. Further, in some production processes using such a polyimide tape, sensors 100 can be produced on both sides of the tape.

Typical embodiments of the invention include an analyte sensing layer disposed on the base layer 102. In a certain embodiment as shown in FIG. 2 the analyte sensing layer comprises a conductive layer 104 which is disposed on insulating base layer 102. In particular, the conductive layer 104 comprises one or more electrodes. The conductive layer 104 can be applied using many known techniques and materials as will be described hereafter, however, the electrical circuit of the sensor 100 is typically defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating protective cover layer 106 such as a polymer coating is typically disposed on portions of the conductive layer 104. Acceptable polymer coatings for use as the insulating protective layer 106 can include, but are not limited to, non-toxic biocompatible polymers such as polyimide, biocompatible solder masks, epoxy acrylate copolymers, or the like. Further, these coatings can be photo-imageable to facilitate photolithographic forming of apertures 108 through to the conductive layer 104. In certain embodiments of the invention, an analyte sensing layer is disposed upon a metallic and/or ceramic and/or polymeric matrix with this combination of elements functioning as an electrode in the sensor.

In the sensor embodiments of the present invention, one or more exposed regions or apertures 108 can be made through the protective layer 106 to the conductive layer 104 to define the contact pads and electrodes of the sensor 100. In addition to photolithographic development, the apertures 108 can be formed by a number of techniques, including laser ablation, chemical milling or etching or the like. A secondary photoresist can also be applied to the cover layer 106 to define the regions of the protective layer to be removed to form the apertures 108. An operating sensor 100 typically includes a plurality of electrodes such as a working electrode and a counter electrode electrically isolated from each other, however typically situated in close proximity to one another. Other embodiments may also include a reference electrode. Still other embodiments may utilize an separate reference element not formed on the sensor. The exposed electrodes and/or contact pads can also undergo secondary processing through the apertures 108, such as additional plating processing, to prepare the surfaces and/or strengthen the conductive regions.

A analyte sensing layer 110 is typically disposed on one or more of the exposed electrodes of the conductive layer 104 through the apertures 108. In particular, the analyte sensing layer 110 is a sensor chemistry layer and most preferably an enzyme layer. Particularly, the analyte sensing layer 110 comprises the enzyme glucose oxidase or the enzyme lactate oxidase. In such embodiments, the analyte sensing layer 110 reacts with glucose to produce hydrogen peroxide which modulates a current to the electrode which can be monitored to measure an amount of glucose present. The sensor chemistry layer 110 can be applied over portions of the conductive layer or over the entire region of the conductive layer. In particular, the sensor chemistry layer 110 is disposed on portions of a working electrode and a counter electrode that comprise a conductive layer. Particular methods for generating the thin sensor chemistry layer 110 include spin coating processes, dip and dry processes, low shear spraying processes, ink-jet printing processes, silk screen processes and the like. Most preferably the thin sensor chemistry layer 110 is applied using a spin coating process.

The analyte sensing layer 110 is typically coated with one or more coating layers. In particular embodiments of the invention, one such coating layer includes a membrane which can regulate the amount of analyte that can contact an enzyme of the analyte sensing layer. For example, a coating layer can comprise an analyte modulating membrane layer such as a glucose limiting membrane which regulates the amount of glucose that contacts the glucose oxidase enzyme layer on an electrode. Such glucose limiting membranes can be made from a wide variety of materials known to be suitable for such purposes, e.g., silicone, polyurethane, polyurea cellulose acetate, Nafion, polyester sulfonic acid (Kodak AQ), hydrogels or any other membrane known to those skilled in the art.

In particular embodiments of the invention, a coating layer is a glucose limiting membrane layer 112 which is disposed above the sensor chemistry layer 110 to regulate glucose contact with the sensor chemistry layer 110. In some embodiments of the invention, an adhesion promoter layer 114 is disposed between the membrane layer 112 and the sensor chemistry layer 110 as shown in FIG. 2 in order to facilitate their contact and/or adhesion. The adhesion promoter layer 114 can be made from any one of a wide variety of materials known in the art to facilitate the bonding between such layers. Preferably, the adhesion promoter layer 114 comprises a silane compound. In alternative embodiments, protein or like molecules in the sensor chemistry layer 110 can be sufficiently crosslinked or otherwise prepared to allow the membrane layer 112 to be disposed in direct contact with the sensor chemistry layer 110 in the absence of an adhesion promoter layer 114.

As noted above, embodiments of the present invention can include one or more functional coating layers. As used herein, the term "functional coating layer" denotes a layer that coats at least a portion of at least one surface of a sensor, more preferably substantially all of a surface of the sensor, and that is capable of interacting with one or more analytes, such as chemical compounds, cells and fragments thereof, etc., in the environment in which the sensor is disposed. Non-limiting examples of functional coating layers include sensor chemistry layers (e.g., enzyme layers), analyte limiting layers, biocompatible layers; layers that increase the slipperiness of the sensor; layers that promote cellular attachment to the sensor; layers that reduce cellular attachment to the sensor; and the like. Typically, analyte modulating layers operate to prevent or restrict the diffusion of one or more analytes, such as glucose, through the layers. Optionally such layers can be formed to prevent or restrict the diffusion of one type of molecule through the layer (e.g. glucose), while at the same time allowing or even facilitating the diffusion of other types of molecules through the layer (e.g. $O_2$). An illustrative functional coating layer is a hydrogel such as those disclosed in U.S. Pat. Nos. 5,786,439 and 5,391,250, the disclosures of each being incorporated herein by reference. The hydrogels described therein are particularly useful with a variety of implantable devices for which it is advantageous to provide a surrounding water layer.

The sensor embodiments disclosed herein can include layers having UV-absorbing polymers. In accordance with one aspect of the present invention, there is provided a sensor including at least one functional coating layer including a UV-absorbing polymer. In particular embodiments, the UV-absorbing polymer is a polyurethane, a polyurea or a polyurethane/polyurea copolymer. More preferably, the selected UV-absorbing polymer is formed from a reaction mixture including a diisocyanate, at least one diol, diamine or mixture thereof, and a polyfunctional UV-absorbing monomer.

UV-absorbing polymers are used with advantage in a variety of sensor fabrication methods, such as those described in U.S. Pat. No. 5,390,671, to Lord et al., entitled "Transcutaneous Sensor Insertion Set"; No. 5,165,407, to Wilson et al., entitled "Implantable Glucose Sensor"; and U.S. Pat. No. 4,890,620, to Gough, entitled "Two-Dimensional Diffusion Glucose Substrate Sensing Electrode", which are incorporated herein in their entireties by reference. However, any sensor production method which includes the step of forming a UV-absorbing polymer layer above or below a sensor element is considered to be within the scope of the present invention. In particular, the inventive method embodiments are not limited to thin-film fabrication methods, and can work with other sensor fabrication methods that utilize UV-laser cutting. Embodiments can work with thick-film, planar or cylindrical sensors and the like, and other sensor shapes requiring laser cutting.

As disclosed herein, the sensor embodiments of the present invention are particularly designed for use as subcutaneous or transcutaneous glucose sensors for monitoring blood glucose levels in a diabetic patient. Typically, each sensor comprises a plurality of sensor elements, for example electrically conductive elements such as elongated thin film conductors, formed between an underlying insulative thin film base layer and an overlying insulative thin film cover layer.

If desired, a plurality of different sensor elements can be included in a single sensor. For example, both conductive and reactive sensor elements can be combined in one sensor, optionally with each sensor element being disposed on a different portion of the base layer. One or more control elements can also be provided. In such embodiments, the sensor can have defined in its cover layer a plurality of openings or apertures. One or more openings can also be defined in the cover layer directly over a portion of the base layer, in order to provide for interaction of the base layer with one or more analytes in the environment in which the sensor is disposed. The base and cover layers can be comprised of a variety of materials, typically polymers. In more specific embodiments the base and cover layers are comprised of an insulative material such as a polyimide. Openings are typically formed in the cover layer to expose distal end electrodes and proximal end contact pads. In a glucose monitoring application, for example, the sensor can be placed transcutaneously so that the distal end electrodes are in contact with patient blood or extracellular fluid, and the contact pads are disposed externally for convenient connection to a monitoring device.

The sensor embodiments of the invention can have any desired configuration, for example planar or cylindrical. The base layer 102 can be self-supportive, such as a rigid polymeric layer, or non-self supportive, such as a flexible film. The latter embodiment is desirable in that it permits continuous manufacture of sensors using, for example, a roll of a polymeric film which is continuously unwound and upon which sensor elements and coating layers are continuously applied.

F. Analyte Sensor Apparatus Configuration Embodiments

In a clinical setting, accurate and relatively fast determinations of analytes such as glucose and/or lactate levels can be determined from blood samples utilizing electrochemical sensors. Conventional sensors are fabricated to be large, comprising many serviceable parts, or small, planar-type sensors which may be more convenient in many circumstances. The term "planar" as used herein refers to the well-known procedure of fabricating a substantially planar structure comprising layers of relatively thin materials, for example, using the well-known thick or thin-film techniques. See, for example, Liu et al., U.S. Pat. No. 4,571,292, and Papadakis et al., U.S. Pat. No. 4,536,274, both of which are incorporated herein by reference. As noted below, embodiments of the invention disclosed herein have a wider range of geometrical configurations (e.g. planar) than existing sensors in the art. In addition, certain embodiments of the invention include one or more of the sensors disclosed herein coupled to another apparatus such as a medication infusion pump.

An exemplary multiple sensor device comprises a single device having a first sensor which is polarized cathodically and designed to measure the changes in oxygen concentration that occur at the working electrode (a cathode) as a result of glucose interacting with glucose oxidase; and a second sensor which is polarized anodically and designed to measure changes in hydrogen peroxide concentration that occurs at the working electrode (an anode) as a result of glucose coming form the external environment and interacting with glucose oxidase. As is known in the art, in such designs, the first oxygen sensor will typically experience a decrease in current at the working electrode as oxygen contacts the sensor while the second hydrogen peroxide sensor will typically experience an increase in current at the working electrode as the hydrogen peroxide generated as shown in FIG. 1 contacts the sensor. In addition, as is known in the art, an observation of the change in current that occurs at the working electrodes as compared to the reference electrodes in the respective sensor systems correlates to the change in concentration of the oxygen and hydrogen peroxide molecules which can then be correlated to the concentration of the glucose in the external environment (e.g. the body of the mammal).

II. Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.: "In Vivo Characteristics of Needle-Type Glucose Sensor-Measurements of Subcutaneous Glucose Concentrations in Human Volunteers," Horm. Metab. Res., Suppl. Ser. 20:17-20 (1988);

Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

III. Methods for Using Analyte Sensor Apparatus Embodiments of the Invention

One embodiment of the invention is a method of sensing an analyte within the body of a mammal, the method including implanting an analyte sensor in to the mammal, the analyte sensor comprising: a plurality of analyte sensor elements that contact and sense analyte; at least one analyte sensor membrane disposed upon at least one of the plurality of analyte sensor elements in a manner that reversibly prevents an analyte from contacting the at least one of the plurality of analyte sensor elements, where the permeability of the analyte sensor membrane can be controlled to allow an analyte to contact at least one of the plurality of analyte sensor elements; and at least one structure operatively coupled to the analyte sensing device for relaying information away from the analyte sensing device; and sensing an analyte within the body of a mammal.

A related embodiment of the invention is a method of sensing an analyte within the body of a mammal, the method including implanting an analyte sensor embodiment disclosed herein in to the mammal and then sensing an alteration in current at the working electrode and correlating the alteration in current with the presence of the analyte, so that the analyte is sensed. Typically, the analyte sensor is polarized anodically such that the working electrode where the alteration in current is sensed is an anode. In one such method, the analyte sensor apparatus senses glucose in the mammal. In an alternative method, the analyte sensor apparatus senses a protein, lactose, a carbohydrate, a saccharide, a mineral, and element, a small molecule compound, a virus, a peptide, a protein fragment, a medication, a drug, an element of a body chemistry assay, body constituent or byproduct lactate, potassium, calcium, oxygen, pH, and/or any physiologically relevant analyte in the mammal.

Certain analyte sensors having the structure discussed above have a number of highly desirable characteristics which allow for a variety of methods for sensing analytes in a mammal. For example in such methods, the analyte sensor apparatus implanted in the mammal functions to sense an analyte within the body of a mammal for more than 1, 2, 3, 4, 5, or 6 months. In particular, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example in both vascular and non-vascular spaces.

IV. Kits and Sensor Set Embodiments of the Invention

In another embodiment of the invention, a kit and/or sensor set, useful for the sensing an analyte as is described above, is provided. The kit and/or sensor set typically includes a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. In particular embodiments, the container holds a plurality of analyte sensing elements, one or more of which is covered by an analyte sensor membrane. The kit and/or sensor set may further include other materials desirable from a commercial and user standpoint, including elements or devices designed to facilitate the introduction of the sensor into the analyte environment, other buffers, diluents, filters, needles, syringes, and package inserts with instructions for use.

Various citations are referenced throughout the specification. In addition, certain text from related art is reproduced herein to more clearly delineate the various embodiments of the invention. The disclosures of all citations in the specification are expressly incorporated herein by reference.

The invention claimed is:

1. A method of sensing an analyte within the body of a mammal, the method comprising implanting an analyte sensor in to the mammal, the analyte sensor comprising:
   a plurality of analyte sensor elements adapted to contact and sense analyte, the analyte sensor elements comprising:
   a base layer;
   at least three working electrodes disposed on the base layer;
   a glucose oxidase layer disposed upon the at least three working electrodes, wherein the least three working electrodes are coated with the glucose oxidase layer so as to allow the analyte sensing device to sense glucose;
   an analyte modulating layer disposed on the glucose oxidase layer, wherein the analyte modulating layer comprises a hydrogel composition that includes a compound selected for its ability to crosslink to a siloxane composition;
   an adhesion promoting layer disposed between the glucose oxidase layer and the analyte modulating layer that functions to promote adhesion between the glucose oxidase layer and the analyte modulating layer, wherein the adhesion promoting layer comprises a siloxane composition crosslinked to the compound in the analyte modulating layer and;
   at least one analyte sensor membrane disposed upon at least one sealable well in a manner that reversibly prevents an analyte from contacting the at least one of the plurality of analyte sensors, wherein the permeability of the analyte sensor membrane can be controlled to allow an analyte to contact at least one of the plurality of analyte sensor elements; and
   at least one structure operatively coupled to the analyte sensing device for relaying information away from the analyte sensing device; and
   sensing an analyte within the body of a mammal.

2. The method of claim 1, further comprising controlling the analyte sensor membrane so that a second analyte sensor element in the plurality of analyte sensor elements contacts analyte after a first analyte sensor element in the plurality of analyte sensor elements exhibits a decrease in the ability to sense analyte due to biofouling, so that the useful life of the analyte sensing device is extended.

3. The method of claim 1, further comprising controlling the analyte sensor membrane so that a second analyte sensor element in the plurality of analyte sensor elements is adapted to contact analyte after a first analyte sensor element in the plurality of analyte sensor elements exhibits a decrease in the ability to sense analyte due to loss of activity of an analyte sensing enzyme disposed in the first analyte sensor element, so that the useful life of the analyte sensing device is extended.

4. The method of claim 1, wherein the analyte sensor membrane comprises a rupturable metallic membrane.

5. The method of claim 4, wherein the analyte sensor membrane hermetically seals the analyte sensor element.

6. The method of claim 1, wherein the analyte sensor membrane comprises a biodegradable polymer.

7. The method of claim 6, wherein the biodegradable polymer is comprised of materials selected for their ability to degrade at a defined rate within an in vivo environment.

8. The method of claim 1, wherein the plurality of analyte sensor elements has a plurality of different analyte sensor membranes disposed thereon.

9. The method of claim 1, further comprising controlling each of plurality of analyte sensor membranes disposed on the analyte sensor elements separately.

10. The method of claim 1, wherein the analyte sensing device is a prolonged analyte sensor.

11. The method of claim 1, wherein the analyte sensing device is a permanent analyte sensor.

12. The method of claim 1, wherein at least two of the analyte sensor elements in the analyte sensing device sense the same analyte.

13. The method of claim 1, wherein at least two of the analyte sensor elements in the analyte sensing device sense different analytes.

14. The method of claim 1, wherein a signal from an individual analyte sensor element within the plurality of analyte sensor elements adapted to contact and sense the analyte in the analyte sensing device is individually interrogated.

15. The method of claim 1, wherein at least one of the analyte sensor elements in the analyte sensing device comprises a hydrogel disposed thereon, wherein upon exposure to an aqueous solution, the hydrogel expands in a manner that increases the permeability of the analyte sensor membrane.

16. A method of extending the useful life of an analyte sensing device comprising analyte sensor elements that exhibit a decrease in the ability to sense analyte over time due to biofouling or a loss of activity of an analyte sensing enzyme disposed on an analyte sensor element; the method comprising sensing an analyte with an analyte sensing device comprising:

a plurality of analyte sensor elements adapted to contact and sense analyte, the analyte sensor elements comprising:
a base layer;
at least three working electrodes disposed on the base layer;
a glucose oxidase layer disposed upon the at least three working electrodes, wherein the least three working electrodes are coated with the glucose oxidase layer so as to allow the analyte sensing device to sense glucose;
an analyte modulating layer disposed on the glucose oxidase layer, wherein the analyte modulating layer comprises a hydrogel composition that includes a compound selected for its ability to crosslink to a siloxane composition;
an adhesion promoting layer disposed between the glucose oxidase layer and the analyte modulating layer that functions to promote adhesion between the glucose oxidase layer and the analyte modulating layer, wherein the adhesion promoting layer comprises a siloxane composition crosslinked to the compound in the analyte modulating layer and;
at least one analyte sensor membrane disposed upon at least one sealable well in a manner that reversibly prevents an analyte from contacting the at least one of the plurality of analyte sensors, wherein the permeability of the analyte sensor membrane can be controlled to allow an analyte to contact at least one of the plurality of analyte sensor elements; and
at least one structure operatively coupled to the analyte sensing device for relaying information away from the analyte sensing device;
wherein the useful life of an analyte sensing device is extended by:
deactivating a first analyte sensor element in the plurality of analyte sensor elements that contact and sense analyte when the first analyte sensing element exhibits a decrease in the ability to sense analyte due to biofouling or a loss of activity of an analyte sensing enzyme disposed on the first analyte sensor element; and
activating a second analyte sensor element in the plurality of analyte sensor elements that contact and sense analyte by controlling the permeability of an analyte sensor membrane disposed upon the second analyte sensor element to allow an analyte to contact the second analyte sensor element, so that the useful life of the analyte sensing device is extended.

* * * * *